United States Patent [19]

Corby, Jr.

[11] Patent Number: 4,664,514

[45] Date of Patent: May 12, 1987

[54] METHOD OF ENHANCING SURFACE FEATURES AND DETECTING SAME

[75] Inventor: Nelson R. Corby, Jr., Scotia, N.Y.

[73] Assignee: General Electric Company, Schenectady, N.Y.

[21] Appl. No.: 668,914

[22] Filed: Nov. 6, 1984

[51] Int. Cl.$^4$ .............................................. G01N 1/30
[52] U.S. Cl. ...................................... 356/36; 356/237
[58] Field of Search .................... 356/36, 38, 445–448, 356/237; 29/558, 26 A; 51/165.72; 901/43, 44, 46, 47, 41; 409/128, 139; 250/459.1; 436/5

[56] References Cited

U.S. PATENT DOCUMENTS

| | | | |
|---|---|---|---|
| 3,734,628 | 5/1973 | Michishita et al. | 360/200 |
| 3,930,407 | 1/1976 | Alburger | 73/104 |
| 4,112,626 | 9/1978 | Watanabe et al. | 51/165.72 X |
| 4,225,228 | 9/1980 | DiMatteo | 356/36 |
| 4,258,264 | 3/1981 | Kotera et al. | 250/459.1 X |
| 4,337,566 | 7/1982 | DiMatteo et al. | 901/47 X |
| 4,349,277 | 9/1982 | Mundy et al. | 356/376 |

OTHER PUBLICATIONS

McGraw-Hill Encyclopedia of Science and Technology, Copyright 1971 by McGraw-Hill, Inc., "Metal Coatings", pp. 335-337 of vol. 8.
"Uncovering Hidden Flaws", by Carl Rain, pp. 49-55, Feb. 1984, High Technology.

*Primary Examiner*—R. A. Rosenberger
*Attorney, Agent, or Firm*—Paul R. Webb, II; James C. Davis, Jr.

[57] ABSTRACT

A method of nondestructive testing of the surface of an object using vapor condensation, such as sputtering, evaporation, or gas disassociation, to lay a thin solid film upon the surface of the object to be tested. The film is either highly reflective or highly absorptive. Portions of the solid film are then removed from the surface, for example, by abrasion while the remaining coating material is in a pattern depending on anomalies. The surface is then irradiated and inspected under light and the differential reflection between the remaining coating material and the surface itself enhances the visibility of the crack or other surface characteristic. The technique is especially useful for detecting very small cracks in cutting or grinding implements made of compacted material.

16 Claims, 4 Drawing Figures

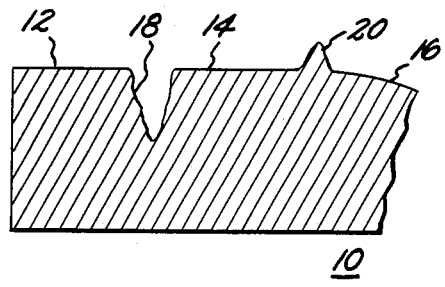
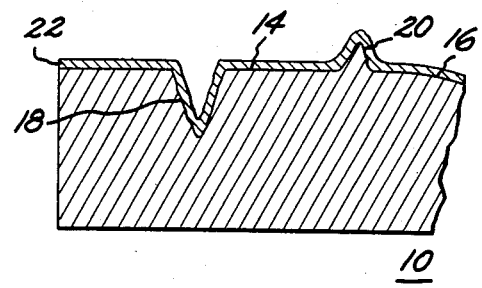
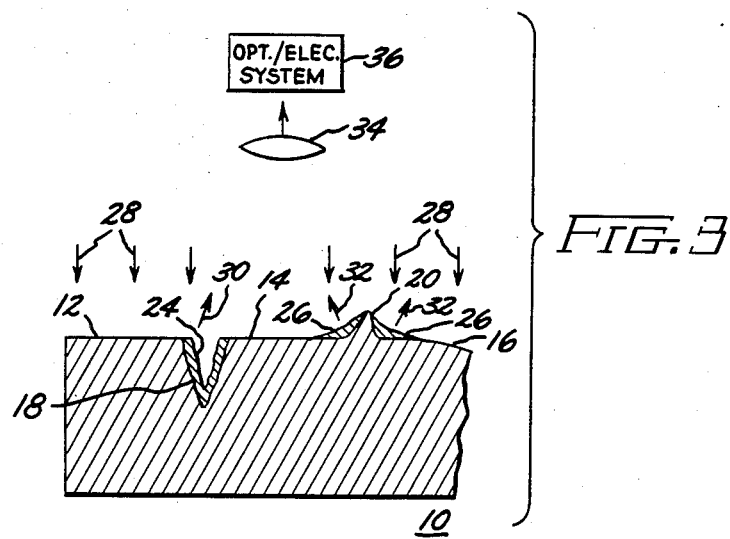
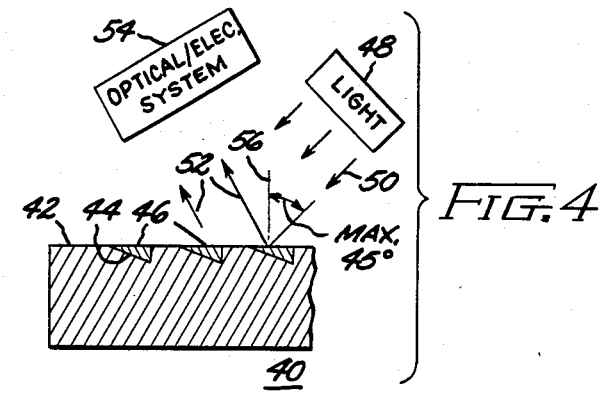

METHOD OF ENHANCING SURFACE FEATURES AND DETECTING SAME

BACKGROUND OF THE INVENTION

This invention relates to methods of nondestructive testing an object wherein physical surface features are enhanced for the purpose of detecting such features.

Surface features are anomalies which are placed intentionally on a surface or surface flaws or defects. It is often necessary to detect anomalies, such as, small surface defects in the form of ridges, cracks, or depressions in aggregated material, for example, diamond compacts or composite cutting tool materials. Occasionally, measurement of the surface defects is required. Some surfaces include cracks less than ½ mil (0.00005 inch) in width and as small as 1 micron (0.000039 inch) in width.

Various techniques have been used for detecting cracks or other small surface depressions. Some techniques use visible dye or fluorescent material carried by a penetrant applied to the surface which is to be tested. The excess is allowed to drip off and/or is shaken loose. Alternately, the surface is washed with water or other liquids or solvents may be applied to the surface. Following the removal of the excess of the liquid dye or fluorescent material, the dye or fluorescent material remains entrapped within surface cracks and makes the surface cracks stand out. Additionally, a developer may be applied to the surface to act as a blotter, thus making the crack more visible.

Instead of using dye or fluorescent material, magnetic particles have been applied to the surface so as to penetrate within those surface cracks which are large enough to receive the particles. The crack causes a non-uniformity in the magnetic field, the non-uniformity being visible from the magnetic particles.

Another method used to locate cracks or other surface flaws has been lighting the surface obliquely (i.e., the light rays being at a small angle relative to the surface) and acquiring a two-dimensional image (by a photograph, tv camera, etc.) of the surface. The existence of a crack may be inferred from detection of a shadowed area caused by the crack.

Although the above techniques of detecting cracks or other depressions in a surface have been generally useful, they have been subject to a number of limitations. Most importantly, such previous techniques have been unable to adequately detect cracks which are less than ½ mil in width. For example, it is difficult to guarantee that the liquid based penetrants will penetrate cracks which are less than ½ mil (about 12.7 microns) in width. Likewise, such cracks are generally too small for detection by magnetic flux techniques and too small to produce an adequate shadow for detection by common oblique lighting.

In addition to the aforenoted difficulties experienced by various known techniques, such prior techniques are limited in other respects. For example, the magnetic flux technique requires a ferromagnetic material. The oblique lighting or shadow technique may be difficult to work satisfactorily if the surface is in extremely dark black.

Another process measures the surface features directly by appropriate interrogating energy sources such as structured light. For example, U.S. Pat. No. 4,349,277 entitled "Non-contact Measurement of Surface Profile", issued Sept. 14, 1982, to Joseph L. Mundy, Gilbert B. Porter and Thomas M. Cipolla, assigned to the assignee of the present invention, discloses a parallax method of surface measurement based upon optical triangulation. The Mundy et al. patent uses alternate beams of different wave length which are applied to the surface of an object. Separate detector rays detect the reflected light to determine the profile of the object. Structured light is difficult to focus to sufficiently small spot sizes over a reasonable depth of field.

Accordingly, it is a primary object of the present invention to provide a new and improved method of enhancement and detection of physical features.

SUMMARY OF THE INVENTION

The above and other objects of the present invention which will become more apparent as the description proceeds are realized by a method of nondestructive testing of the surface of an object, the steps comprising: applying a coating material of a solid film to a surface of the object, the coating material having different reflective properties from the surface, the coating material being applied by a process which allows penetration and deposition at least within all depressions as small as 1 micron in width, removing at least part of the solid film of coating material such that remaining coating material is within surface depressions; subjecting the surface and remaining coating material to electromagnetic radiation; and inspecting the surface for depression by checking for differences in electromagnetic properties between the surface and any remaining coating material.

Preferably, the surface inspection is by testing the differential reflection of electromagnetic radiation between the surface and any remaining coating material. Abrasion is used to remove at least part of the solid film of coating material such that the coating material remains in surface depressions. The coating material may be applied to the surface by application of particles, substantially all of which have a size below 100 nanometers. The coating material may be applied to the surface by a process of vapor condensation and is highly reflective of electromagnetic radiation such as light. Depressions in the surface are detected by checking for high light reflection. The coating material consists essentially of metal and the method is particularly effective for testing sintered compacts of material.

The present invention may alternately be described as a method of nondestructive testing an object, the steps comprising: applying a solid film of coating material to a surface of the object, the coating material having different electromagnetic reflective properties from the surface, the coating material being applied by a process which ensures penetration and deposition within at least all depressions as small as 1 micron in width on the surface; removing at least part of the solid film from the surface such that remaining coating material is in a pattern dependent on anomalies on the surface; subjecting the surface and any remaining coating material to electromagnetic radiation; and inspecting the surface for anomalies by checking for differences in electromagnetic properties between the surface and any remaining coating material.

Preferably, the surface inspection is by checking for differential reflection of electromagnetic radiation between the surface and any remaining coating material. The coating material is highly reflective of light, the electromagnetic radiation is light, and anomalies are detected by checking for high light reflection while the coating material consists essentially of an elemental metal and the object tested is a sintered compact of material. The coating material may be applied to the surface by vapor condensation to ensure application of particles, substantially all of which have a size of below 100 nanometers. Instead of a reflective coating, the solid film may have alternating layers which comprise an optical interference filter.

The present invention may alternately be described as a method of nondestructive testing an object, the steps comprising: applying a metallic coating to a surface of the object, the coating applied such that it is deposited within all depressions as small as 1 micron in width on the surface and forms into highly reflective metallic solid film on the surface; removing at least part of the solid film from the surface such that remaining coating material is in a pattern dependent on anomalies on the surface; shining light on the surface including portions covered by any remaining coating material; and inspecting the surface for anomalies by checking for differential reflection of light between the surface and any covered portions. Preferably, the removing step allows coating material to remain in surface depressions, if any, and abrasion is used to accomplish the removal step. The coating material consists essentially of an elemental metal and the object tested is a sintered compact of material. The coating material is applied to the surface by a process of vapor condensation. The coating material is applied to the surface by gas disassociation vapor deposition.

The present invention may alternately be described as a method of testing an object, the steps comprising: applying coating material to a surface of the object, the coating material applied to the surface by a process of vapor condensation, the coating material applied such that it is deposited within depressions, if any, on the surface and forms into a solid film on the surface; removing at least part of the solid film from the surface such that remaining coating material, if any, is in pattern dependent on anomalies, if any, on the surface; subjecting the surface including portions covered by any remaining coating material to electromagnetic radiation; and inspecting the surface for anomalies by checking for differences in electromagnetic radiation caused by differences in electromagnetic properties between the object itself and any remaining coating material. The coating material may be applied to the surface by a process of evaporation of the coating material followed by its condensation on the surface. Alternately, the coating material is applied to the surface by a process of sputtering. Alternately, the coating material is applied to the surface by gas disassociation vapor deposition. Abrasion is used to accomplish the removal step. The surface is inspected by checking for differential reflection of electromagnetic radiation between the surface and any remaining covered portions. The coating material is applied by a process providing for penetration and deposition at least within all cracks, if any, on the surface as small as ½ mil in width, and the removing step allows the coating material to remain in cracks on the surface. The coating material is metallic and highly reflective of light, the electromagnetic radiation is light, and depressions are detected by checking for high light reflection.

BRIEF DESCRIPTION OF THE DRAWINGS

The above and other features of the present invention will be more readily understood when the following detailed description is considered in conjunction with the accompanying drawings wherein like reference characters represent like parts throughout the several views and in which:

FIG. 1 shows a cross-section view of a portion of an object which is to be nondestructively tested.

FIG. 2 shows the object of FIG. 1 after a solid film of coating material has been applied to one of its surfaces.

FIG. 3 shows the object of FIG. 2 after part of the solid film has been removed from the surface, the object being under an optical inspection system; and FIG. 4 shows a cross-section view of a portion of an alternate object with its surface features enhanced by the present method and with a schematic illustration of an alternate optical inspection system.

DETAILED DESCRIPTION

FIG. 1 shows a fragmentary cross-section side view of a portion of an object 10 having a surface 12 which is to be tested for surface anomalies by use of the present method. The surface 12 may include a part 14 which is flat and a curved surface past 16. The surface 12 has two anomalies shown, a crack 18 and ridge 20. It should be apparent that FIG. 1 is only a representative illustration for purposes of description. In actuality, a surface may have many flaws. Also, the drawings are shown in highly magnified form for purposes of illustration of the flaws, many of which have dimensions less than 1 micron.

Although the present method is especially well adapted to detecting depressions, such as crack 18, within a surface, the method is broadly applicable towards the detection of other surface features including both features which are planned and flaws. Thus, the anomalies in FIG. 1 might be features which are intentionally included on the surface 12 such as a machined groove. Alternately, and more likely, the anomalies appear in the form of a very small surface flaw such as crack 18 or ridge 20.

The present method will work for testing numerous types of objects, but the present method is especially well adapted for use on industrial parts such as industrial grits, cutting tool faces, diamond compacts, and the like which are subject to abrasion during their use. Accordingly, the description which follows will consider that the object 10 is a cutting tooth made as a sintered compact of tungsten-carbide and having a blackish-grey color.

In order to enhance the visibility of the features of surface 12, coating material is applied to the surface 12 to form a solid film 22 as shown in FIG. 2. If necessary, the surface could be cleaned prior to the application of the coating material. Significantly, the coating material making up the solid film 22 is applied by a process which allows penetration and deposition at least within all depressions, if there are any surface depressions, on the surface 12 which are as small as 1 micron in width. This will allow the detection of cracks which are quite small. The solid film 22 should have electromagnetic reflectance properties different from the object itself. For a highly absorptive object such as the black tungsten-carbide compact, the coating material should be a highly reflective material such as aluminum, gold or other reflective metal. The penetration and deposition of the solid film 22 within the quite small cracks, is made certain by application of the solid film 22 by a process of vapor condensation. The vapor condensation could be any of at least three well known processes for application of a thin, usually specular, coating upon a surface. The three different processes of vapor condensation are well known in the art and need not be discussed in detail herein. Vapor condensation includes the evaporation process wherein coating material is applied to a surface by a process of evaporation of the coating material followed by its condensation upon the surface. Usually, the coating material evaporates from a pool of molten metal within a chamber placed at a low pressure and having a high temperature. The molten metal evaporated from the pool condenses upon the desired surface or surfaces of the object. The object which is to be coated may have a voltage applied to it in order to attract the usually metallic vapor particles.

A second type of vapor condensation process is known as sputtering or cathode sputtering. This process relies upon a high voltage discharge between electrodes within a chamber which is typically filled with inert gas. The object which is to be coated is used as one electrode and particles from the other electrode are deposited thereon.

A third, and probably best, process which may be used with the present method is commonly called chemical vapor deposition and uses gas disassociation in order to coat an object. This gas disassociation technique, which is quite well known within the semiconductor manufacturing field, includes the placement of gas within a chamber having a high temperature and a relatively low pressure. Upon further lowering of the pressure, bonds of the vapor molecules will be severed such that atoms from the molecules will be applied to a surface or surfaces of an object placed within the chamber. The object will be coated by the atoms which form into a solid film.

Although any of the above three types of vapor condensation processes could be used, the gas disassociation or chemical deposition process may well be the simplest and most efficient in penetrating into the smallest cracks within a surface. To ensure adequate penetration of cracks with the evaporation and sputtering processes, it may be advisable to repeat each of these processes more than once such that the relative position between the source, such as, the molten metal in the evaporation technique, or the electrode in the sputtering technique, and the target or object is changed. These considerations are of course known to those in the art. In addition to the simplicity of not requiring a second deposition step, the gas disassociation or chemical vapor deposition process proceeds faster than the other two methods.

It should be noted that any of the three above discussed vapor condensation processes apply the coating material by deposition of particles having a size at least below 100 nanometers and down to the diameter of a single atom. By use of such small particles, these processes may easily penetrate and deposit particles within cracks or other depressions having a width as small as 1 micron.

Since most of the solid film 22 will be abraded off the surface 12 as discussed below, it is preferable for the solid film 22 to be as thin as possible consistent with penetration of the small cracks and relatively uniform thickness. The gas disassociation or chemical vapor deposition coating process will provide relatively uniform thicknesses in a coating which is as thin as 1 micron. Accordingly, with reference to FIG. 2, the crack 18 might have a width at its top of ½ mil and the thickness of the solid film 22 may be 3 microns. As illustrated in FIG. 2 the solid film 22 penetrates crack 18 and conforms to the side walls and bottom of the crack 18 and is quite uniform in thickness. Thus, the solid film 22 may conform to the top surface 12 including conformity to crack 18 due to use of the vapor condensation application process.

With reference now to FIG. 3, object 10 is shown after at least part of the solid film 22, as shown in FIG. 2 has been removed such that the remaining portions of the coating material, which includes portion 24 within crack 18 and portions 26 on each side of ridge 20, are in a pattern dependent upon anomalies on the surface 12. Although various processes could be used for removal of most of the solid film 22, as shown in FIG. 2, it is preferable to use an abrasion process such as grit tumbling, sand blasting, grinding, polishing using a mild abrasive, wire brushing, or shot peening. Any of these techniques will leave the coating material in portions such as 24 within small cracks such as 18. Depending upon the material from which object 10 is made, these mechanically abrasive processes may additionally leave some of the coating material in portions such as 26 adjacent the ridge 20. Of course, if it is desired, the process can be sufficiently abrasive to grind down the ridge 20 whereby portions 26 would also be removed and would no longer be disposed upon part 16 of surface 12.

Assuming that the object 10 is a hard surface tool as used for cutting or is otherwise subject to mechanical abrasion during its usage, the abrasion used to remove most of the solid film 22, as shown in FIG. 2, will most likely not significantly modify the object 10. Of course, other objects which could withstand abrasion techniques are suitable for use in the present method for nondestructive testing. Although abrasion is highly preferred as the step for removal of the parts of solid film 22 overlying the smooth portions of surface parts 14 and 16, other removal methods could be used provided that such methods leave the solid coating material within surface cracks.

Following the selective removal of most of the film 22 such that the film or coating material remains in portions 24 and 26, as shown in FIG. 3, surface 12 is subjected to electromagnetic radiation, more specifically diffuse light rays 28, only some of which are labeled in FIG. 3. Although the light source is preferably approximately normal to the surface 12, it will be appreciated that any arrangement of one or more diffuse light sources (not shown) may be used to fully illuminate the surface 12. Preferably, the coating material remaining within solid film portions 24 and 26 is aluminum, gold, or other highly reflective metal. Accordingly, the light 28 striking the portions 24 and 26 will be reflected back in light rays 30 and 32 respectively. This reflected light may be visible to the human eye either with or without a microscope, depending upon the size of the portions 24 and 26. If the tungsten-carbide material used for the cutting tooth or object 10 is extremely dark, the differential reflectivity between those portions of surface 12 which are uncovered and those portions which are still covered by the coating material, portions 24 and 26, will have a large differential in their reflectivity.

Instead of visual inspection of the surface 12 for depressions or other anomalies as revealed by the pattern of remaining coating material, a lens 34 and optical-electrical system 36 may be used to detect the differential reflectivity between the uncovered portions of surface 12 and the coating material 24 and 26. It will be readily appreciated that numerous types of optical-electrical systems may be used for system 36 including tv cameras, regular cameras, or various types of imaging systems. Accordingly, the specifics of the system 36 need not be discussed in detail. However, it should be noted that the system 36 may also be a non-imaging type of system which simply integrates the reflected light received from the surface 12. If sufficient reflected light is received from the surface 12, this indicates the presence of anomalies sufficiently large to cause the industrial part or object 10 to fail the test. A non-imaging system may be used for system 36 because it is often unnecessary to know the exact location of the crack 18. The presence of the crack 18 may be sufficient to indicate that the part or object 10 is unsuitable for use.

As shown in FIG. 3, the abrasion or other process used to remove most of the coating material will not remove the coating material within crack 18 or on the sides of ridge 20. The ridge 20 might alternately be detected by removing only a very small portion of the solid film 22, as shown in FIG. 2, such that the solid film 22 would remain covering the surface 12 except that ridge 20 would be uncovered. The ridge 20 could thus be detected by looking for a place of low reflectivity, assuming that the coating material 22 is highly reflective, at least 10% more reflective than the object 10 itself. Alternately, coating material 22 might have a lower reflectivity than the surface 12 itself and the inspection system 36 or the human viewing the surface 12 might look for a highly reflective ridge 20 extending above an otherwise solid film of less reflective coating. Of course, abrading the surface 12 with coating 22 disposed thereon only sufficiently to expose the ridge 20 would not allow one to detect the crack 18. Regardless of how complete the abrading process is, it will be appreciated that the remaining coating material will be disposed in a pattern dependent upon anomalies on surface 12.

Turning now to FIG. 4, there is shown an object 40 having a surface 42 including small grooves 44 which are covered or filled with coating material portions 46. The coating material portions 46 are the remaining portions of a solid film which was deposited and selectively removed in the same fashion as with the process performed on the object 20. The remaining coating material 46 may be highly reflective such that light 48 directs light rays 50 at the surface 42 whereupon portions 46 reflect light rays 52 to an optical-electronic system 54 which detects the reflected rays 52. The system 54 may be disposed behind a lens (not shown) such as lens 34 of FIG. 3. The object 40 of FIG. 4 is different from the object 10 in that the surface features, grooves 44, which are detected are intentionally included within the surface 42. The light 48, which may be relatively diffuse or could even be a scanning laser light, is disposed such that light rays 50 are within 45 degrees of the line 56 which is normal to surface 42. The system 54 is disposed to best receive the reflected rays 52 based upon the well-known principle that the angle of incidence is equal to the angle of reflection.

Concisely describing an example of the present method, a tungsten-carbide cutting tooth 10 is placed in a chemical vapor deposition chamber and is coated with a 3 micron layer of aluminum by use of gas disassociation. The aluminum particles applied to the surface or surfaces are significantly less than 100 nanometers and the coating is deposited on the surface or surfaces which are under test including depressions as small as 1 micron in width. The surface or surfaces which have been coated and are to be tested are then sandblasted. The surface or surfaces are then inspected for anomalies by checking for differences in electromagnetic radiation caused by differences in electromagnetic properties between the tungsten-carbide of the object itself and any remaining aluminum. Specifically, light is shined upon the surface or surfaces and the highly reflective aluminum, if any remains, stands out in the blackish-gray sintered compacted tungsten-carbide. The reflectivity indicative of surface cracks may appear by visual inspection using a microscope or, alternately, be detected by an optical-electrical system. The optical-electrical system uses a computer to integrate the light over the surface or surfaces in question and reject the part as unsuitable if a sufficiently large amount of light is reflected from the surface or surfaces. Of course, if the sandblasting has removed substantially all of the aluminum, virtually no light will be reflected, that is mirror-type reflection, not diffuse reflection, and the tooth will be acceptable as not having troublesome surface cracks.

The present method might alternately be used upon a boron nitrite cutting tooth which is generally white in color. For example, copper or tantalum would be applied to the surface or surfaces which are to be tested. The metal would be applied by chemical vapor deposition or other appropriate coating process. Upon removal of the coated object from the chamber in which it was coated, the metal coating can be made to oxidize and change its color and reflectivity. The surface or surfaces are then subjected to sandblasting so as to selectively remove most of the metal oxide on the surfaces. The oxide which remains within any cracks in the boron nitrite cutting tooth will be of lower reflectivity than the surfaces of the cutting tooth.

The present method might use optical interference layers as an alternative to the specular reflection layers discussed above. For example, a surface which is to be tested may have multiple extremely thin layers of magnesium fluoride vacuum deposited upon the surface which is to be tested. As well-known in the optical arts, this alternating layer arrangement realizes an optical interference filter. The filter may cause constructive interference so as to be highly reflective at a particular light frequency. Alternately, the thickness of the layers may be such as to make the interference filter or reflector cause destructive interference so as to be highly anti-reflective or absorptive at a particular light frequency. In either case, the alternating thin layers may be applied to the surface which is to be tested. The coated surface may then be abraded or otherwise subject to removal of at least part of the solid film comprised of the alternating layers. The surface would then be subject to light at the frequency of constructive interference, for the highly reflective interference filter or at the frequency of destructive interference, for the anti-reflective filter. The differences in reflective properties between the object itself and any remaining coating material comprising interference portions may be used to detect surface cracks, depressions, or other anomalies.

While the invention has been particularly described with reference to preferred steps, it will be understood by those skilled in the art that various changes in form and details may be made therein without departing from the spirit and scope of the present invention.

What I claim as new and desire to secure by Letters Patent of the United States is:

1. A method of nondestructive testing of a surface of an object, the steps comprising:

coating the surface of an object with a solid film of coating meterial having different reflective properties from said surface, said coating material being applied by vapor deposition with substantially all of the particles having a size below 100 nanometers which ensures penetration and deposition at least within all depressions as small as 1 micron width on said surface;

removing at least part of said solid film of coating material from said surface; retaining said coating material within depresssions on said surface;

thereafter irradiating said surface and any remaining coating material with electromagnetic radiation; and inspecting said irradiated surface for depressions by checking for differences in electromagnetic properties between said surface and any remaining coating material.

2. The method of claim 1 wherein the step of inspecting said irradiated surface for depressions is by testing the differential reflection of electromagnetic radiation between said surface and any remaining coating material.

3. The method of claim 2 wherein said coating material is highly reflective of light, said electromagnetic radiation is light, and depressions are detected by checking for high light reflection.

4. The method of claim 3 wherein said coating material consists essentially of metal.

5. The method of claim 4 wherein said object is a sintered compact of material.

6. The method of claim 1 wherein the step of removal of said at least part of the solid film of coating material is by abrasion.

7. A method of nondestructive testing of a surface of an object the steps comprising:

coating the surface of the object with a solid film of coating material having different electromagnetic reflective properties form said surface, said coating material being applied by vapor deposition with substantially all of the particles having a size below 100 nanometers which ensures depressions as small as 1 micron in width on said surface;

removing at least part of said solid film from said surface; retaining the remaining coating material in a pattern dependent on anomalies on said surface;

subjecting said surface and any remaining coating material to electromagnetic radiation; and inspecting said surface for anomalies by checking for differences in electromagnetic properties between said surface and any remaining coating material.

8. The method of claim 7 wherein the step of inspecting said surface for anomalies is by checking for differential reflection of electromagnetic radiation between said surface and any remaining coating material.

9. The method of claim 8 wherein said coating material is highly reflective of light, said electromagnetic radiation is light, and anomalies are detected by checking for high light reflection.

10. The method of claim 9 wherein said coating material consists essentially of an elemental metal.

11. The method of claim 10 wherein said object is a sintered compact of material.

12. The method of claim 7 wherein said solid film has alternating layers which comprise an optical interference filter.

13. The method of claim 7 wherein said vapor deposition is gas disassociation vapor deposition.

14. A method of nondestructive testing of a surface of an object, the steps comprising:

coating the surface of the object with a metallic coating material, said coating material applied by vapor deposition with substantially all of the particles having a size below 100 nanometers such that it is deposited within all depressions as small as 1 micron in width on said surface and forms into a highly reflective metallic solid film on said surface;

removing at least part of said solid film from said surface; retaining the remaining coating material in a pattern dependent on anomalies present on the surface;

shining light on said surface including portions covered by any remaining coating material; and inspecting said surface for anomalies by checking for differential reflection of light between said surface and any remaining coating material.

15. The method of claim 14 wherein the removal step comprises subjecting the surface to abrasion.

16. The method of claim 14 wherein said coating material consists essentially of an elemental metal and said object is a sintered compact of material.

* * * * *